US012085716B2

(12) United States Patent
Lychagov et al.

(10) Patent No.: US 12,085,716 B2
(45) Date of Patent: Sep. 10, 2024

(54) EYE ACCOMMODATION DISTANCE MEASURING DEVICE AND METHOD FOR HEAD-MOUNTED DISPLAY, AND HEAD-MOUNTED DISPLAY

(71) Applicant: Samsung Electronics Co., Ltd., Suwon-si (KR)

(72) Inventors: Vladislav Valerievich Lychagov, Saratov (RU); Vladimir Mikhailovich Semenov, Malakhovka (RU); Evgeniia Yurievna Salamatova, Volgograd (RU)

(73) Assignee: Samsung Electronics Co., Ltd., Suwon-si (KR)

( * ) Notice: Subject to any disclaimer, the term of this patent is extended or adjusted under 35 U.S.C. 154(b) by 483 days.

(21) Appl. No.: 17/581,352

(22) Filed: Jan. 21, 2022

(65) Prior Publication Data

US 2022/0155599 A1 May 19, 2022

Related U.S. Application Data

(63) Continuation of application No. PCT/KR2020/008766, filed on Jul. 6, 2020.

(30) Foreign Application Priority Data

Sep. 12, 2019 (RU) ................................ 2019128648
Apr. 7, 2020 (KR) ......................... 10-2020-0042405

(51) Int. Cl.
*G02B 27/01* (2006.01)
*G01B 9/02001* (2022.01)
(Continued)

(52) U.S. Cl.
CPC ..... *G02B 27/0172* (2013.01); *G01B 9/02004* (2013.01); *G01B 9/02007* (2013.01);
(Continued)

(58) Field of Classification Search
CPC .............. G02B 27/017; G02B 27/0172; G02B 27/0176; G02B 2027/0174;
(Continued)

(56) References Cited

U.S. PATENT DOCUMENTS 7,769,419 B2 * 8/2010 Daly .................. A61B 5/14532
600/316
8,437,008 B2 5/2013 Fercher et al.
(Continued)

FOREIGN PATENT DOCUMENTS

CN 101668475 A 3/2010
CN 102421352 A 4/2012
(Continued)

OTHER PUBLICATIONS

Chinese Office Action dated Jul. 4, 2022, issued in Chinese Patent Application No. 202010659541.0.
(Continued)

*Primary Examiner* — Bao-Luan Q Le
(74) *Attorney, Agent, or Firm* — Jefferson IP Law, LLP

(57) ABSTRACT

An eye accommodation distance determining device is provided. The eye accommodation distance determining device includes an interferometer configured to generate a plurality of frequency modulated laser beams in different directions and to generate a plurality of interferometric signals using laser beams reflected from eye reflecting surfaces, a signal processer configured to generate a signal spectrum using each of said plurality of interferometric signals, a distance determiner configured to determine distances to the eye reflecting surfaces for each of said plurality of frequency modulated laser beams, a point coordinates determiner configured to determine coordinates of points on each of the eye reflecting surfaces for each of the laser beams, a reconstructor configured to generate an eye inner structure model
(Continued)

based on the determined coordinates of points, and an eye accommodation distance determiner configured to determine, based on said eye inner structure model, an eye accommodation distance.

15 Claims, 13 Drawing Sheets

(51) Int. Cl.
    *G01B 9/02004*      (2022.01)
    *G01S 7/4915*      (2020.01)
    *G01S 17/34*      (2020.01)
    *G06T 19/00*      (2011.01)

(52) U.S. Cl.
    CPC ............ *G01S 7/4915* (2013.01); *G01S 17/34* (2020.01); *G06T 19/006* (2013.01)

(58) Field of Classification Search
    CPC ........ G02B 2027/0178; G01B 9/02004; G01B 9/02007; G01S 7/4915; G01S 17/34; G06T 19/006
    See application file for complete search history.

(56) References Cited

U.S. PATENT DOCUMENTS

| | | | |
|---|---|---|---|
| 9,220,404 B2* | 12/2015 | Ng | A61F 2/16 |
| 9,649,024 B2* | 5/2017 | Hacker | G01B 9/02091 |
| 9,652,034 B2 | 5/2017 | He et al. | |
| 9,906,781 B2 | 2/2018 | Fujimaki | |
| 10,154,254 B2 | 12/2018 | Trail | |
| 10,209,519 B2 | 2/2019 | Vieira et al. | |
| 10,241,329 B2 | 3/2019 | Perreault et al. | |
| 10,254,547 B2 | 4/2019 | Tremblay et al. | |
| 10,485,416 B2* | 11/2019 | Ng | A61B 3/0025 |
| 10,849,493 B2* | 12/2020 | Copland | A61B 3/10 |
| 11,026,575 B2* | 6/2021 | Raymond | G01B 9/02091 |
| 11,112,613 B2* | 9/2021 | Lanman | G02B 27/0093 |
| 11,156,829 B2* | 10/2021 | Zhang | G09G 3/006 |
| 11,156,835 B2* | 10/2021 | Samec | G16H 50/20 |
| 11,625,095 B2* | 4/2023 | Konrad | G06F 3/165 345/156 |
| 11,751,763 B2* | 9/2023 | Copland | A61B 3/107 351/221 |
| 11,963,722 B2* | 4/2024 | Copland | A61B 3/0025 |
| 2007/0078308 A1* | 4/2007 | Daly | A61B 3/10 600/587 |
| 2008/0074615 A1 | 3/2008 | Lai et al. | |
| 2008/0208022 A1 | 8/2008 | Kruger et al. | |
| 2011/0149245 A1 | 6/2011 | Barth et al. | |
| 2011/0176113 A1 | 7/2011 | Ho et al. | |
| 2012/0069298 A1* | 3/2012 | Ng | A61B 3/18 351/205 |
| 2012/0113092 A1 | 5/2012 | Bar-Zeev et al. | |
| 2013/0301009 A1* | 11/2013 | Hacker | G01B 9/02091 351/246 |
| 2014/0375541 A1 | 12/2014 | Nister et al. | |
| 2015/0070273 A1 | 3/2015 | He et al. | |
| 2015/0235431 A1 | 8/2015 | Schowengerdt | |
| 2015/0235469 A1 | 8/2015 | Schowengerdt | |
| 2016/0071435 A1* | 3/2016 | Ng | A61B 3/0025 434/271 |
| 2016/0270656 A1* | 9/2016 | Samec | A61B 3/1216 |
| 2016/0370605 A1 | 12/2016 | Ain-Kedem | |
| 2017/0109562 A1 | 4/2017 | Shroff et al. | |
| 2017/0124928 A1 | 5/2017 | Edwin et al. | |
| 2018/0045965 A1 | 2/2018 | Schowengerdt | |
| 2018/0092524 A1* | 4/2018 | Ng | G09B 23/30 |
| 2018/0205943 A1 | 7/2018 | Trail | |
| 2018/0242840 A1* | 8/2018 | Copland | A61B 3/1005 |
| 2019/0187482 A1* | 6/2019 | Lanman | G02B 26/105 |
| 2019/0223714 A1* | 7/2019 | Raymond | G01B 9/02004 |
| 2021/0026069 A1* | 1/2021 | Baets | G02B 27/0087 |
| 2021/0033856 A1* | 2/2021 | Zhang | G02B 27/0081 |
| 2021/0076935 A1* | 3/2021 | Copland | A61B 3/101 |
| 2022/0156995 A1 | 5/2022 | Harrises et al. | |
| 2022/0236796 A1* | 7/2022 | Konrad | G09G 3/002 |
| 2022/0322933 A1* | 10/2022 | Copland | A61B 3/113 |
| 2022/0330813 A1* | 10/2022 | Raymond | A61B 3/102 |

FOREIGN PATENT DOCUMENTS

| | | |
|---|---|---|
| CN | 105934902 A | 9/2016 |
| CN | 106062665 A | 10/2016 |
| CN | 106170729 A | 11/2016 |
| RU | 2 656 714 C2 | 6/2018 |
| RU | 2 671 298 C2 | 10/2018 |
| WO | 2018/077868 A1 | 5/2018 |
| WO | 2018/178336 A1 | 10/2018 |

OTHER PUBLICATIONS

Chinese Office Action dated Apr. 2, 2022, issued in Chinese Patent Application No. 202010659541.0.
International Standard, Safety of Laser Products, IEC 60825-1, Aug. 2001.
Xu et al., Proceedings of the Tenth International Conference on Management Science and Engineering Management, 2017.
International Search Report dated Oct. 8, 2020, issued in International Patent Application No. PCT/KR2020/008766.
Russian Office Action dated Feb. 12, 2020, issued in Korean Patent Application No. 2019128648.
Russian Notice of Allowance dated Apr. 23, 2020, issued in Korean Patent Application No. 2019128648.

* cited by examiner

EYE ACCOMMODATION DISTANCE MEASURING DEVICE AND METHOD FOR HEAD-MOUNTED DISPLAY, AND HEAD-MOUNTED DISPLAY

CROSS-REFERENCE TO RELATED APPLICATION(S)

This application is a continuation application, claiming priority under § 365(c), of an International application No. PCT/KR2020/008766, filed on Jul. 6, 2020, which is based on and claims the benefit of a Russian patent application number 2019128648, filed on Sep. 12, 2019, in the Russian Intellectual Property Office, and of a Korean patent application number 10-2020-0042405, filed on Apr. 7, 2020, in the Korean Intellectual Property Office, the disclosure of each of which is incorporated by reference herein in its entirety.

BACKGROUND

1. Field

The disclosure relates to the field of stereoscopic displays. More particularly, the disclosure relates to an eye accommodation distance measuring device and a method for a head-mounted display as well as to corresponding head-mounted display and may be used in augmented/virtual reality systems (AR/VR).

2. Description of Related Art

Physiological principles of three dimension (3D) objects perception in the real world require matching of eye focus (i.e., accommodation distance) and eye convergence point (i.e., vergence distance). In commercial AR/VR systems, having fixed focal length, these values cannot be matched, which causes so called vergence-accommodation conflict (VAC) and, as a result, fatigue and visual discomfort for a user. When using AR-glasses, VAC effect significantly complicates a process of matching real and virtual objects since when observing the real object, the virtual object may be defocused. This problems could be mitigated by automatic eye focus measurements (tracking) and providing feedback to AR glasses rendering system.

Further, there is a problem of defocusing due to eye movement. Typically overview in the virtual reality is done by head rotations, whereas in the real world it also could be done by eye movement. In conventional AR/VR systems eye movement lead to a destruction of a rendered picture. A solution providing eye tracking is required to solve this problem.

One of the main augmented reality (AR) systems problems is focus matching for real and artificial objects. If virtual images co-located with real world objects are in different focal planes, a disparity in blur forces the user to change focus upon gazing at objects that should be completely sharp.

Thus, there is a need for cheap and compact gaze direction and eye focusing tracking device that is able to be integrated into AR/VR device (e.g., AR glasses, VR helmets). Additional requirements for such device is eye safety for user and small delay in measuring eye accommodation distance (e.g., high measuring speed).

Known from the prior art is an eye tracking system disclosed in document US 2014375541 A1. The known system uses time of flight (TOF) camera to acquire two dimensional (2D) image of human eye, track gaze direction and to determine distance to display. The known system is only for gaze direction tracking, no information about eye accommodation distance is acquired. TOF cameras have drawback of dead zones at low distance from camera, which potentially leads to complicated design.

Known from the prior art is an eye tracking device disclosed in document US 2017109562 A1. The known device uses depth sensor to measure curvature of eye front surface to estimate the gaze direction. The known device is only for gaze direction tracking, no information about eye accommodation distance is acquired.

Known from the prior art is a laser optical feedback tomography (LOFT) sensor disclosed in document US 20080208022 A1. The known sensor improves efficiency of laser self-mixing interferometry (SMI) performance by frequency shifting optical feedback to laser relaxation oscillations frequency. Drawbacks of the known sensor consist in using beam splitter, frequency shifter and mechanical scanning. Document US 20080208022 A1 does not disclose sensor implementations suitable for AR/VR devices or intended for eye tracking.

Known from the prior art is head-mounted display (HID) disclosed in document U.S. Ser. No. 10/154,254 A1. The known display includes an eye tracking system, which is based on the usage of TOF camera. The eye tracking system includes an illumination source, an imaging device and a controller. The controller determines depth information related to eye surfaces and generates a model of the eye. The known display is mostly focused on gaze direction tracking. Drawbacks of the display are complicated signal processing based on image processing of temporal distorted light patterns. As noted above, TOF cameras have drawback of dead zones at low distance from camera, which potentially leads to complicated design.

Known from the prior art is a device for vision correction using eye tracking and depth detection disclosed in document US 2016370605 A1. The known device includes wearable computing device having a variable lens, an eye tracking sensor, and a depth sensor. The known device estimates depth of focus indirectly and does not provide desired accuracy.

Known from the prior art is a display system disclosed in document US 2017124928 A1. The known system may capture images of a projected light field, and determine focus depths (or lateral focus positions) for various regions of the light field using the captured images. The system is capable to correct various display imperfections and aberrations. Image is constructed at various focal depths. The system is based on eye-tracking and does not involve depth or eye focus tracking.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide an eye accommodation distance measuring device and a method for a head-mounted display.

Another aspect of the disclosure is to provide a head-mounted display that may be used in augmented/virtual reality systems.

Additional aspects will be set forth in part in the description which follows and, in part, will be apparent from the description, or may be learned by practice of the presented embodiments.

In accordance with an aspect of the disclosure, an eye accommodation distance determining device is provided. The eye accommodation distance determining device includes an interferometer configured to generate a plurality of frequency modulated laser beams in different directions and to generate a plurality of interferometric signals using laser beams reflected from eye reflecting surfaces among the plurality of frequency modulated laser beams, a signal processer configured to generate a signal spectrum using each of the plurality of interferometric signals, a distance determiner configured to analyze the signal spectrum and determine distances to the eye reflecting surfaces for each of the plurality of frequency modulated laser beams, a point coordinates determiner configured to determine coordinates of points on each of the eye reflecting surfaces for each of the plurality of frequency modulated laser beams based on the determined distances to the eye reflecting surfaces and laser beam direction information, a reconstructor configured to generate an eye inner structure model based on the determined coordinates of points on the eye reflecting surfaces, and an eye accommodation distance determiner configured to determine, based on the eye inner structure model, an eye accommodation distance.

Each of signal spectra generated for laser beams falling on retina of an eye by the signal processor may have first to fourth peaks in a frequency domain, the first peak may correspond to a cornea surface, the second peak may correspond to a lens front surface, the third peak may correspond to a lens rear surface, and the fourth peak may correspond to a retina surface.

The distance determiner may be further configured to extract peaks according to optical path distances of laser beams from the first to fourth peaks of each of the signal spectra in the frequency domain and calculate distances to the eye reflecting surfaces reflecting each of the plurality of frequency modulated laser beams.

The plurality of frequency modulated laser beams may fall into different points on the eye reflecting surfaces, and the signal processor may be further configured to generate signal spectra for the different points on the eye reflecting surfaces using the plurality of frequency modulated laser beams.

The reconstructor may be further configured to calculate a cornea curvature radius, a lens front surface curvature radius, a lens rear surface curvature radius, a lens thickness, and a distance between lens and retina by approximating points corresponding to a cornea surface, a lens front surface, and a lens rear surface into spherical surfaces and to determine, based thereon, an eye accommodation distance.

The reconstructor may be further configured to determine a direction of an eye optical axis as a direction of a line at which centers of the approximating spherical surfaces are located.

The signal processor, the distance determiner, the point coordinates determiner, the reconstructor, and the eye accommodation distance determiner may be implemented as single software, a single semiconductor chip, or a single electronic circuit.

The interferometer may be a self-mixing interferometer including a laser array including a plurality of frequency modulated lasers and a laser array driver configured to supply each laser of the laser array with a frequency-modulated control signal, and the interferometric signal may be a laser self-mixing signal.

The interferometer may be a self-mixing interferometer including a laser, a laser driver configured to supply the laser with a frequency-modulated control signal, and an optical-mechanical scanning system, and the interferometric signal may be a laser self-mixing signal.

The interferometer may be configured to direct laser beams, reflected from the eye reflecting surfaces, back to a cavity of a laser emitting the plurality of frequency modulated laser beam.

The interferometer may include a laser array including a plurality of lasers, a laser array driver configured to supply each laser of the laser array with a frequency-modulated control signal, a detector, a beam-splitter, and a reference mirror, and the interferometric signal may be a signal generated by the detector.

The interferometer may include a laser, a laser driver configured to supply the laser with a frequency-modulated control signal, a detector, a beam-splitter, a reference-mirror, and an optical-mechanical scanning system.

The beam-splitter may be configured to divide a laser beam emitted by laser into a first beam and a second beam, the first beam may be reflected from the reference-mirror, the second beam may be reflected from eye reflecting surfaces, and the reflected first beam and the reflected second beam may form an interferometric signal in the detector.

In accordance with another aspect of the disclosure, an eye accommodation distance determining method is provided. The eye accommodation distance determining method includes generating a plurality of frequency modulated laser beams in different directions, wherein a beam direction information corresponds to each of beam direction, wherein at least part of said plurality of beams strikes upon reflecting surfaces of an eye inner structure, generating an interferometric signal for each beam of the plurality of frequency modulated laser beams, generating a signal spectrum for each interferometric signal of the plurality of interferometric signals, analyzing the signal spectrum and determining distances to reflecting surfaces for each beam of the plurality of frequency modulated laser beams, determining, in a coordinate system associated with the head-mounted display, coordinates of points of eye surfaces for each of the beams based on the determined distances to the reflecting surfaces and the beam direction information, generating an eye inner structure model based on the determined coordinates of points of eye surfaces, determining, based on the eye inner structure model, an eye accommodation distance.

In accordance with another aspect of the disclosure, an adjustable focal length head-mounted display is provided. The adjustable focal length head-mounted display includes the eye accommodation distance determining device and an adjustable focal length rendering system, wherein the adjustable focal length rendering system is configured to automatically adjust focal length based on an eye accommodation distance obtained from the eye accommodation distance determining device.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

The same reference numerals are used to represent the same elements throughout the drawings.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
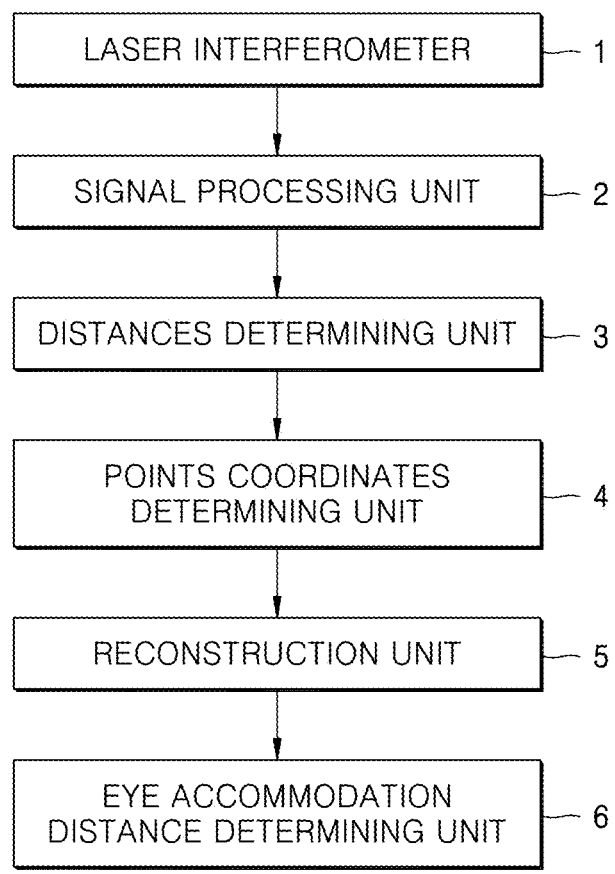
FIG. 1 depicts a block diagram of an eye accommodation distance determining device according to an embodiment of the disclosure.

FIG. 1 depicts a block diagram of an eye accommodation distance determining device according to an embodiment of the disclosure.

Referring to FIG. 1, an eye accommodation distance determining device for head-mounted display, according to an embodiment, comprises a laser interferometer 1, a signal processing unit 2, a distance determining unit 3, a point coordinates determining unit 4, a reconstruction unit 5, and an eye accommodation distance determining unit 6. In FIG. 1, the signal processing unit 2, the distance determining unit 3, the point coordinates determining unit 4, the reconstruction unit 5, and the eye accommodation distance determining unit 6 are separately illustrated for convenience of description, but the signal processing unit 2, the distance determining unit 3, the point coordinates determining unit 4, the reconstruction unit 5, and the eye accommodation distance determining unit 6 may be actually implemented as single software, a single semiconductor chip, or a single electronic circuit.

The laser interferometer 1 generates a plurality of frequency modulated laser beams in different directions forming a beam bundle and detects a light reflected from one or more surfaces of an eye, including surfaces of eye outer and inner structures, generating an interferometric signal for each beam. For example, the surfaces of the eye outer structures are surfaces of cornea or sclera, and the surfaces of the eye inner structures are surfaces of lens or retina.

The signal processing unit 2 perform processing of the interferometric signals and generating a signal spectrum for each signal of the plurality of interferometric signals generated by the laser interferometer.

Spectra of signals of beams reflected from the eye structure surfaces have specific peaks with different frequencies corresponding to reflections from different surfaces.

Figure 2:
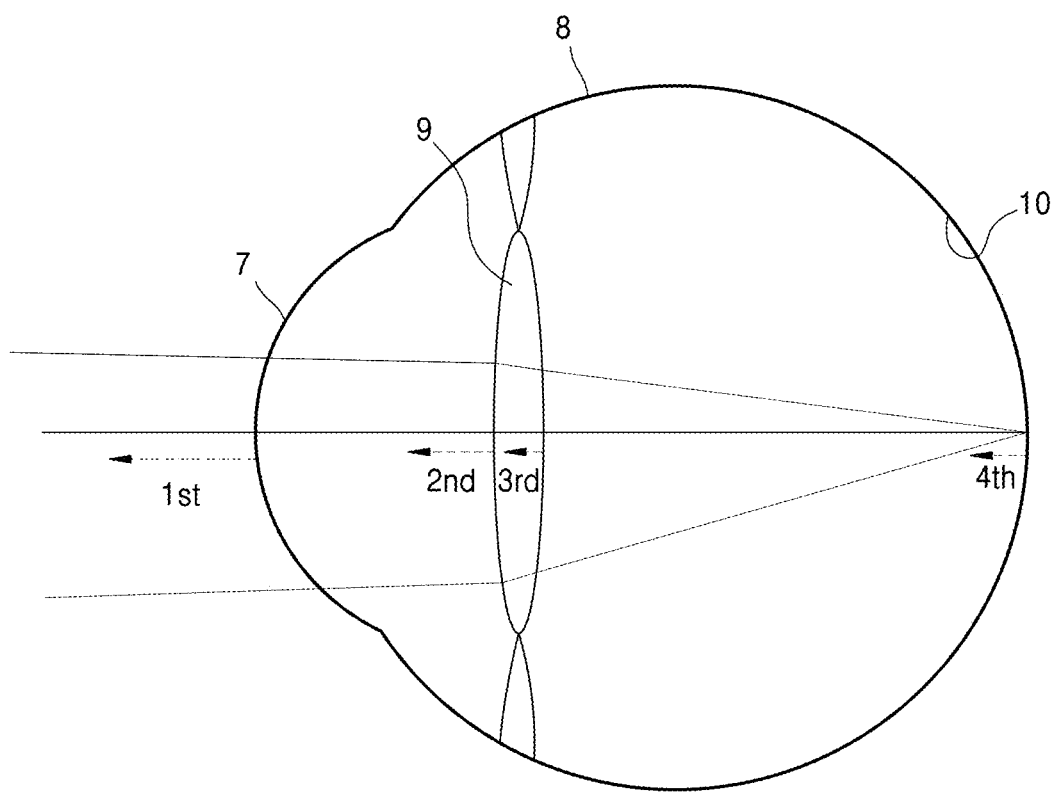
FIG. 2 depicts a schematic diagram illustrating an eye inner structure that reflects a laser beam according to an embodiment of the disclosure.

FIG. 2 depicts a schematic diagram illustrating an eye inner structure that reflects a laser beam according to an embodiment of the disclosure.

Figure 3:
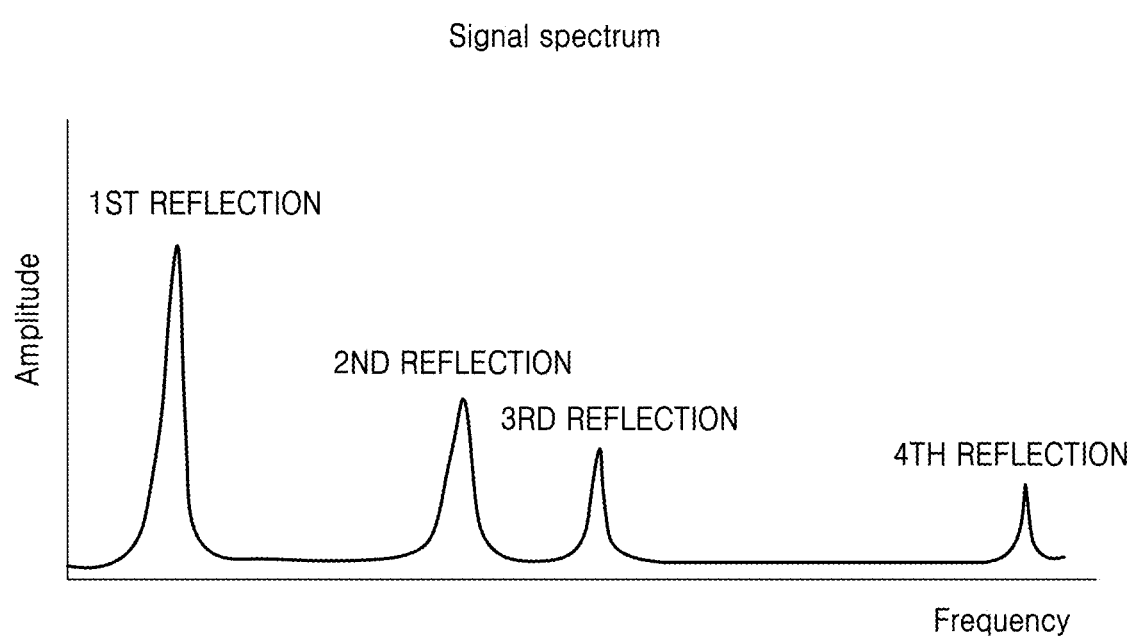
FIG. 3 depicts an example of signal spectra generated by laser beams reflected from eye structure surfaces according to an embodiment of the disclosure.

FIG. 3 depicts an example of signal spectra generated by laser beams reflected from eye structure surfaces according to an embodiment of the disclosure.

Referring to FIGS. 2 and 3, spectra of signals of beams that fall into an eye pupil will have four peaks with different frequencies corresponding to reflections from the reflecting surfaces of the inner and outer eye structures, namely from a surface of the cornea 7 or the sclera 8, a front surface of the lens 9, a rear surface of the lens 9 and a surface of the retina 10. Thus, the spectrum peaks may be interpreted as different reflecting surfaces. For example, a first peak corresponds to the surfaces of the cornea 7 and the sclera 8 of the eye, a second peak corresponds to the iris and front surface of the lens 9, a third peak corresponds to the rear surface of the lens 9, and a fourth peak corresponds to the surface of the retina 10 of the eye.

The distance determining unit 3 performs, for each laser beam, a signal spectrum analysis using interferometry techniques and determines one or more distances to one or more surfaces reflecting the laser beam.

Figure 4:
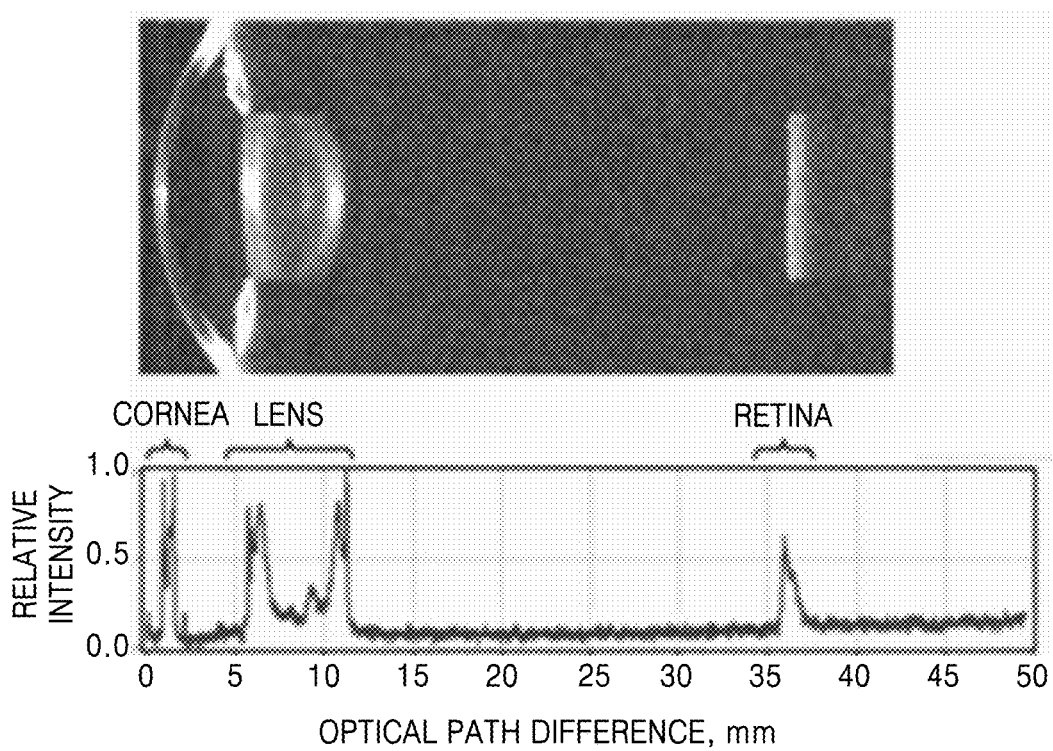
FIG. 4 depicts an interpretation of a beam interferometric signal spectrum showing distances to eye structure reflecting surfaces according to an embodiment of the disclosure.

FIG. 4 depicts an interpretation of a beam interferometric signal spectrum showing distances to eye structure reflecting surfaces according to an embodiment of the disclosure.

Referring to FIG. 4, the distance determining unit 3 extracts four peaks according to optical path distances from four peaks in a frequency domain depicted in FIG. 3 through a signal spectrum analysis and calculates distances between surfaces reflecting each of the laser beams.

The point coordinates determining unit 4 determines, based on an information about distances to reflecting surfaces for each beam and an information about beam direction (about a position of the beam in space), in a coordinate system associated with the head-mounted display, coordinates of points of eye structure surfaces. Each point may be related to specific surface of the eye structure. For example, a laser beam falling on the retina 10 of the eye among laser beams has four reflections. In this case, a first point of the signal spectrum corresponds to a point on the cornea surface, a second point of the signal spectrum corresponds to a point on the lens front surface, a third point of the signal spectrum corresponds to a point on the lens rear surface, a fourth point of the signal spectrum corresponds to a point on the retina surface. For a beam with two reflections, a first peak of the signal spectrum corresponds to the cornea surface, and a second peak of the signal spectrum corresponds to the iris surface. For a beam with one reflection, a single peak corresponds to the sclera, the sclera surface, or another surface (if the beam does not fall on the user's eye).

Figure 5:
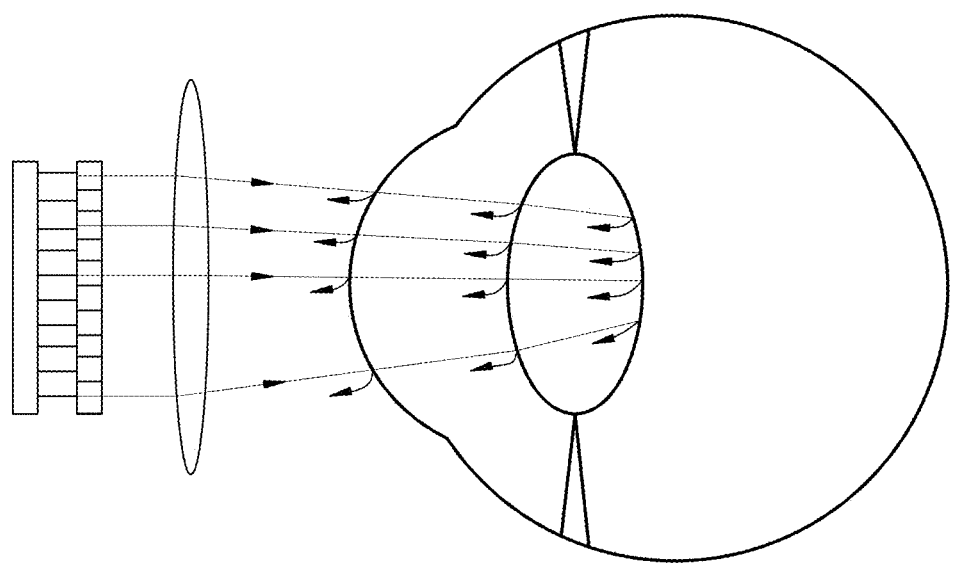
FIG. 5 depicts an example of a plurality of beams reflected from an eye structure reflecting surfaces according to an embodiment of the disclosure.

FIG. 5 depicts an example of a plurality of beams reflected from an eye structure reflecting surfaces according to an embodiment of the disclosure.

Figure 6:
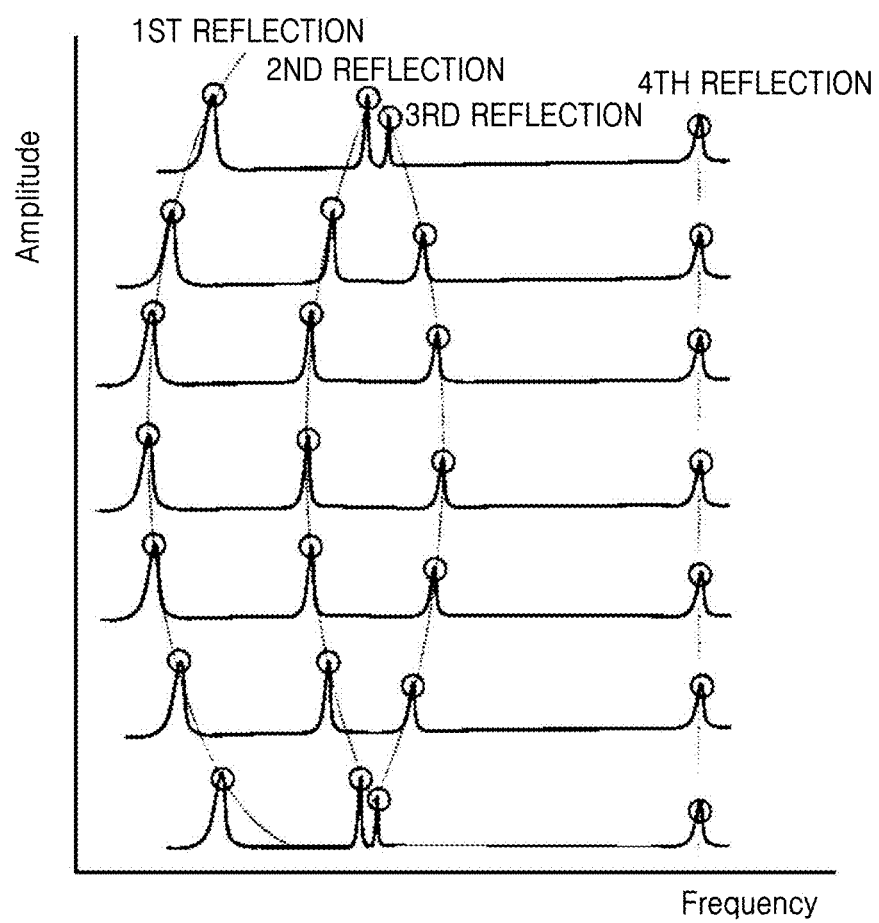
FIG. 6 schematically depicts interferometric signals spectra of a plurality of beams reflected from an eye structure surfaces according to an embodiment of the disclosure.

FIG. 6 schematically depicts interferometric signals spectra of a plurality of beams reflected from an eye structure surfaces according to an embodiment of the disclosure.

Referring to FIG. 5, a plurality of frequency modulated laser beams fall on different points on eye structure surfaces. Referring to FIG. 6, positions of first to fourth peaks of a signal spectrum in the frequency domain are changed according to positions of the points on the eye structure surfaces on which the plurality of frequency modulated laser beams are incident. The signal processing unit 2 generates signal spectra for different points on the eye structure surfaces using the plurality of frequency modulated laser beams. The distance determining unit 3 determines distances between surfaces on propagation paths of the plurality of laser beams using the plurality of signal spectra obtained from the plurality of laser beams. The point coordinates determining unit 4 may determine coordinates of different points on the eye structure surfaces using information provided from the distance determining unit 3.

The reconstruction unit 5 generates, based on an information about eye structure surfaces information, an eye structure model. The eye structure model may be generated, for example, by approximating points by geometric surfaces. For example, groups of points corresponding to the cornea surface, the lens front surface and the lens rear surface may be approximated by spherical surfaces, and the group of points related to retina may be approximated by a plane. Thus, the eye structure model may be a combination of approximating surfaces corresponding to the surfaces of eye structure elements.

The reconstruction unit may be configured to determine a direction of an eye optical axis as a direction of a line at which centers of approximating spherical surfaces corresponding to the eye structure surfaces are located.

The eye accommodation distance determining unit 6 determines, based on the eye inner structure model, an eye accommodation distance.

Figure 7:
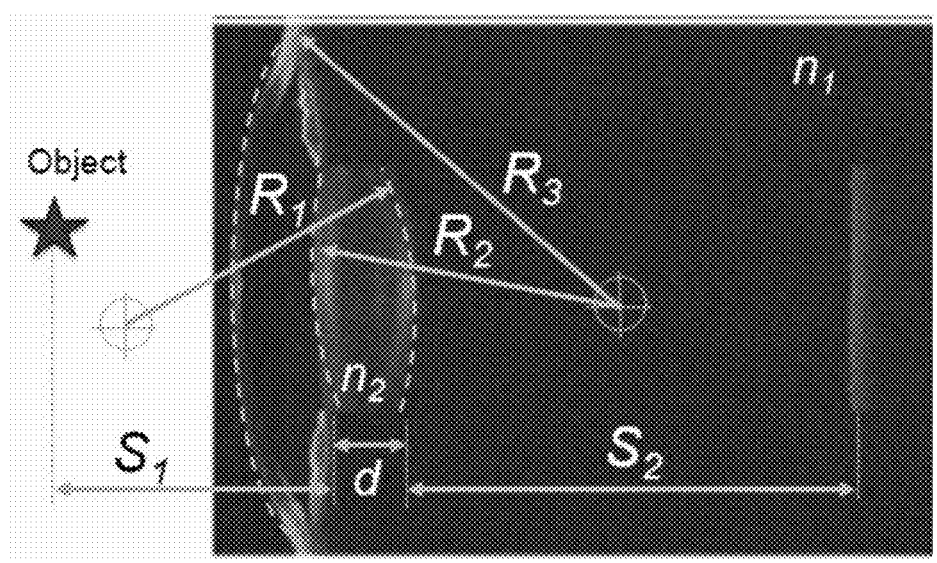
FIG. 7 depicts a model of eye inner structure according to an embodiment of the disclosure.

FIG. 7 depicts a model of eye inner structure according to an embodiment of the disclosure.

Figure 8:
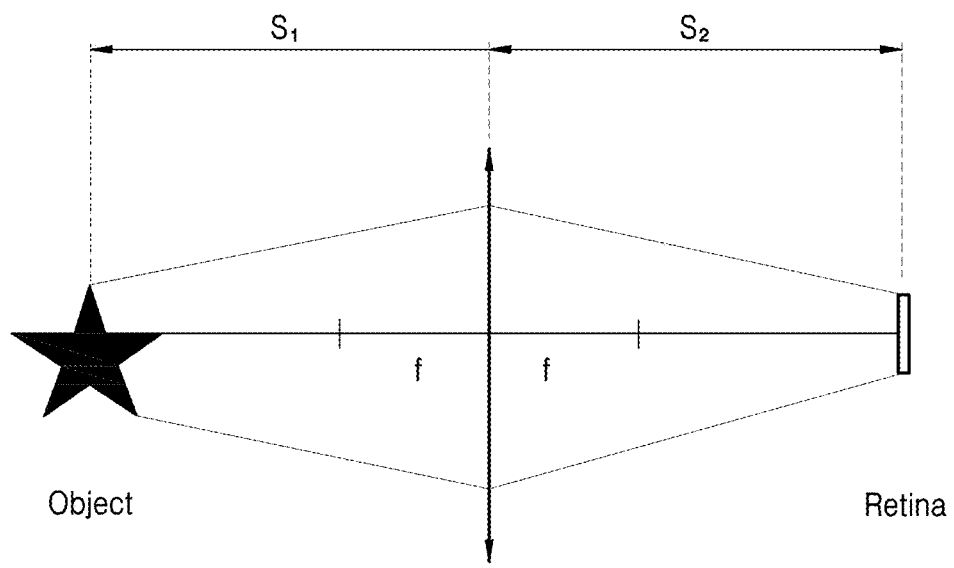
FIG. 8 depicts an eye effective optical layout according to an embodiment of the disclosure.

FIG. 8 depicts an eye effective optical layout according to an embodiment of the disclosure.

Referring to FIGS. 7 and 8, the eye accommodation distance (S1) may be determined based on distances between the eye structure surfaces (S2, d) and curvatures of said surfaces (R1-1, R2-1, R3-1), which may be obtained based on the eye structure model generated by the reconstruction unit. Accommodation distance (S1) may be determined from the following combination of equations:

$$\frac{1}{S_1} + \frac{1}{S_2} = \frac{1}{f} \quad \text{Equation 1}$$

$$\frac{1}{f} = (n_2 - n_1)\left(\frac{1}{R_2} + \frac{1}{R_1} + \frac{(n_2 - n_1)d}{n_2 R_1 R_2}\right) \quad \text{Equation 2}$$

Where:
(1)—thin lens equation (effective optical layout equation);
(2)—eye optical system equation;
f—effective optical layout focal length;
R1—cornea curvature radius;
R2—lens front surface curvature radius;
R3—lens rear surface curvature radius;
d—lens thickness;
S1—accommodation distance (is to be calculated);
S2—distance between lens and retina;
n1—eye media refractive index (of a vitreous body); and
n2—lens media refractive index.

Among the above mentioned values, values R1, R2, R3, d and S2 are determined based on the eye inner structure model (see FIG. 7), values n1 and n2 are predetermined, value S1 is to be determined.

Thus, the proposed device provides precise eye accommodation distance determination based on the eye inner structure model.

Specific embodiments differing in ways of generating interferometric signals and in ways of generating the plurality of frequency modulated laser beams in different directions are set forth below.

First Embodiment

Figure 9:
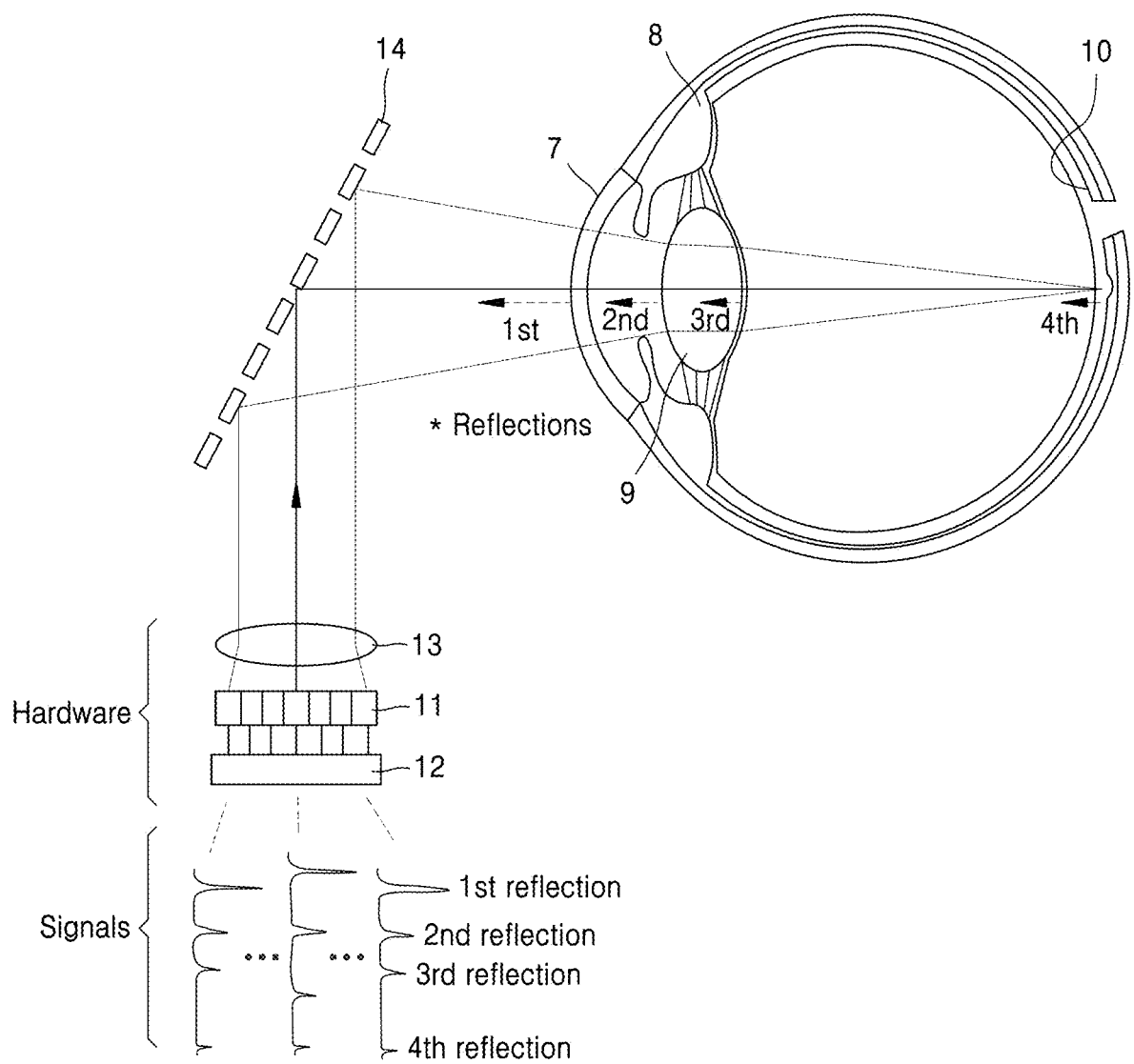
FIG. 9 depicts schematic diagram of an eye accommodation distance determining device according to an embodiment of the disclosure.

FIG. 9 depicts schematic diagram of an eye accommodation distance determining device according to an embodiment of the disclosure.

Referring to FIG. 9, the interferometer of the eye accommodation distance determining device is a self-mixing interferometer (SMI) and comprises a laser array 11, for example, an array of vertical-cavity surface-emitting lasers (VCSEL), a laser array driver 12 and an optical system.

The laser array driver 12 selectively supplies a frequency modulated control signal providing modulation of a laser pump current to lasers of the array, simultaneously to one laser, group of laser or to all the lasers of the laser array 11. A number of simultaneously operating lasers is limited by a maximum allowable laser radiation power safe for the eye. Each laser of the array has specific beam direction which is different from others, is known in advance and depends from a location of the laser of the laser array 11 relative to other parts of the eye accommodation distance determining device involved in forming the beam direction.

The optical system is involved in forming directions of the beams, provides transportation of a radiation to a user's eye and may comprise, for example, one or more lenses 13 and a dichroic mirror 14. The dichroic mirror is just one example of solution providing transportation of the radiation to the user's eye. Alternatively, for example, a waveguides may be used.

In the scope of the disclosure, term beam direction is to be understood as a location, in a space, relative to the coordinate system associated with the head-mounted display, of an axis of the laser beam on a last part of its propagation path before falling on the eye reflecting surfaces, i.e., on a part of the beam propagation path after its exit from the optical system of the interferometer.

According to the embodiment, the interferometer generates self-mixing interferometric signal. A beam emitted by specific laser is delivered to the eye via elements of the optical system, is reflected by the eye structure surfaces, enters back to a cavity of the laser emitting the laser beam and affects its generation mode (self-mixing effect occurs). These effect is detected by measuring laser bias voltage on the driver side or by measuring laser power oscillations using photodiode (not shown in the figures) built in a laser package. A corresponding signal obtained from driver or photodiode is a self-mixing interferometric signal.

Thus, the laser array is used to generate the plurality of beams and the SMI effect is used to generate the interferometric signal. The embodiment is characterized by a minimum number of elements, simple construction and low cost.

Here and in other embodiments, functions of generating the plurality of beams and delivering the radiation to the user's eye and corresponding elements (e.g., the optical system and an optical-mechanical scanning system) are conditionally related to the interferometer, although, if required, may be considered separately.

Second Embodiment

Figure 10:
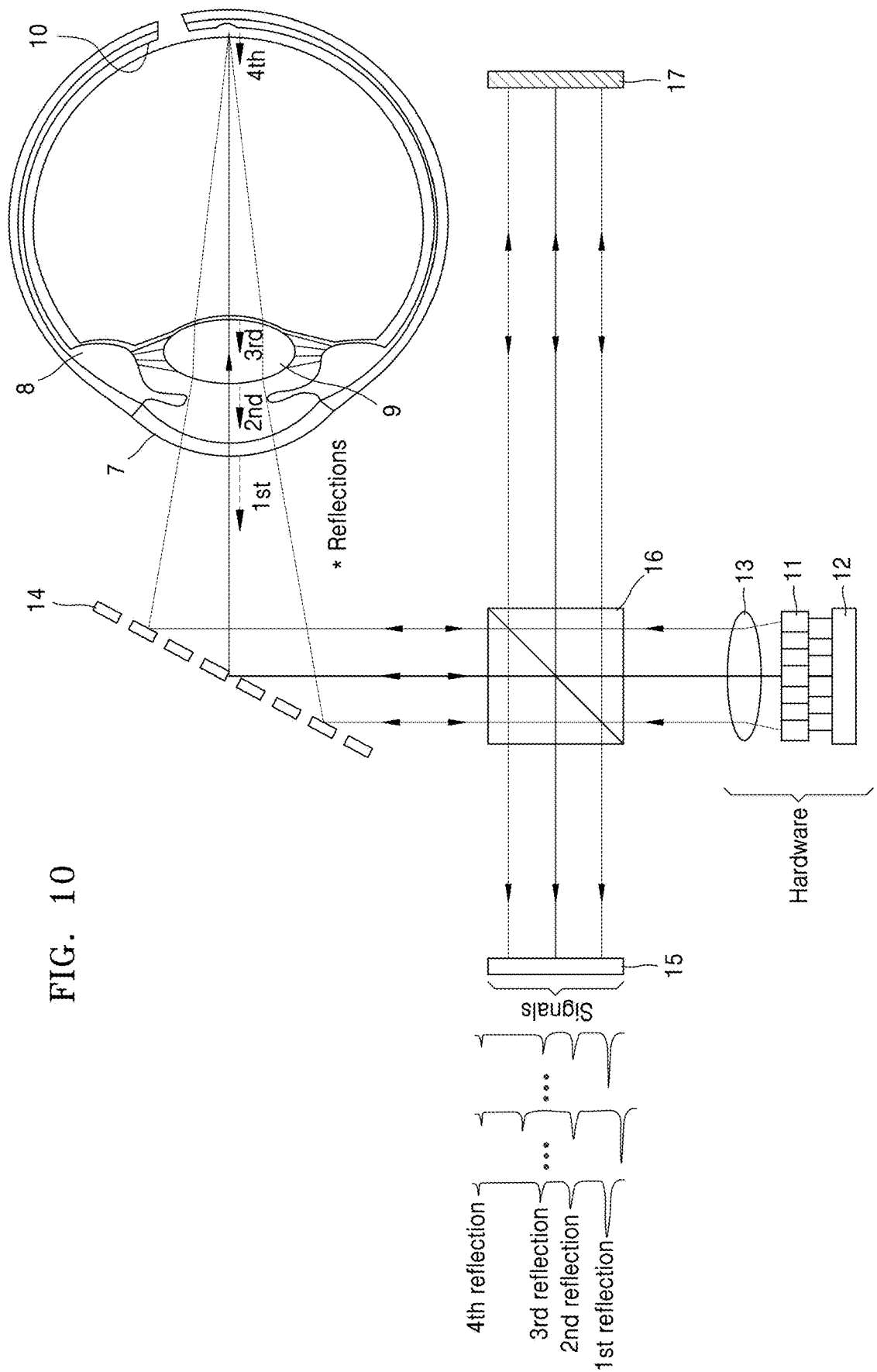
FIG. 10 depicts schematic diagram of an eye accommodation distance determining device according to an embodiment of the disclosure.

FIG. 10 depicts schematic diagram of an eye accommodation distance determining device according to an embodiment of the disclosure.

Referring to FIG. 10, the interferometer of the eye accommodation distance determining device is a two-arm interferometer comprising a laser array 11, a laser array driver 12, a detector 15, a beam splitter 16, a reference mirror 17 and an optical system.

The laser array, the laser array driver and the optical system correspond to those of the first embodiment and are not described again.

The second embodiment differs from the first one in a method of generating the interferometric signal. A beam emitted by specific laser of the array is divided by the beam splitter 16 (partially reflecting mirror) into two beams, one of which reflects from the reference mirror 17 and the other one is delivered to the user's eye and reflects from its surfaces. Both beams return to beam splitter 16 and are sent to detector 15 (see FIG. 10), wherein they interfere and form an interferometric signal.

The embodiment has more parts, is less compact and more expensive, but provides better signal to noise ratio with the same laser power.

Third Embodiment

Figure 11:
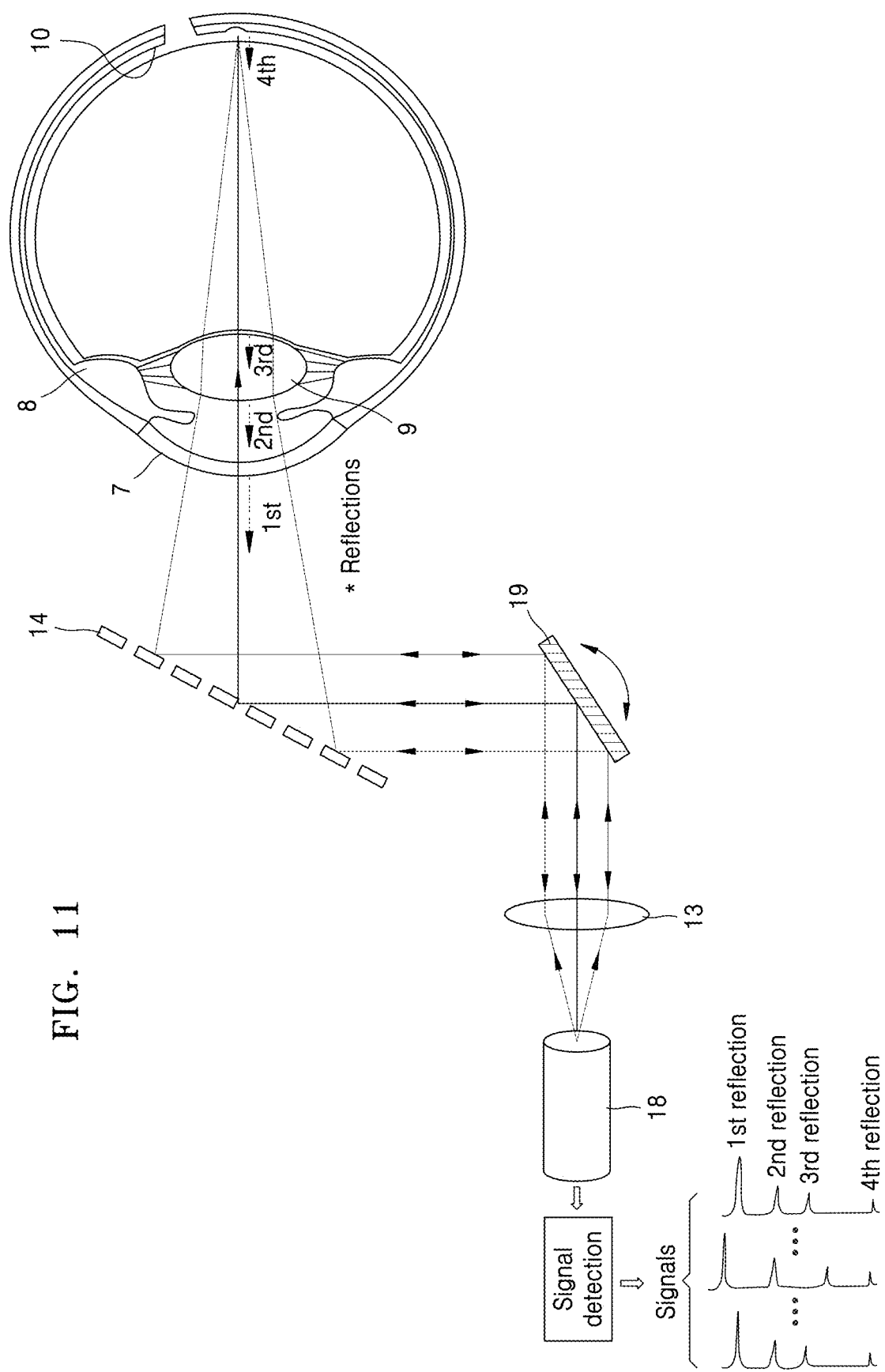
FIG. 11 depicts schematic diagram of an eye accommodation distance determining device according to an embodiment of the disclosure.

FIG. 11 depicts schematic diagram of an eye accommodation distance determining device according to an embodiment of the disclosure.

Referring to FIG. 11, the interferometer of the eye accommodation distance determining device is a self-mixing interferometer and comprises a single laser 18, a laser driver, an optical-mechanical scanning system and an optical system.

The optical system of the disclosure corresponds to that of the previous embodiments and is not described again.

Generation of the interferometric signal is performed using self-mixing effect similarly to the first embodiment, namely by measuring laser bias voltage on the driver side or by measuring laser power oscillations using photodiode built in a laser package.

Optical-mechanical scanning system provides change of the laser beam direction and may be implemented using any state of art light deflecting technique, for example, using a rotational mirrors, Micro-Electro-Mechanical Systems (MEMS) mirrors, movable lens, acousto optic deflectors, etc. In the example of the considered embodiment schematically illustrated in FIG. 11, an element of the optical-mechanical scanning system is a movable mirror 19.

Optical-mechanical scanning system, for example, may comprise a system of movable mirrors actuated by motors and providing laser beam scanning, mirror position sensors and a controller that controls the motors, reads sensors and provides generation of a signal characterizing a state of the scanning system at each moment of time and allowing to determine the laser beam position at each moment of time (i.e., the beam direction information).

Regarding the embodiment, wherein the optical-mechanical scanning system is used, since a single laser is used, the beam of which can continuously move in space, a specific laser beam should be understood as a laser beam considered within a small time interval (e.g., within a modulation period of the laser), in which the position of the beam in space changes in a negligible manner, and the set of beams should be understood as a set of specific beams considered among a plurality of small intervals of time. The embodiment is less robust and more bulky.

Fourth Embodiment

Figure 12:
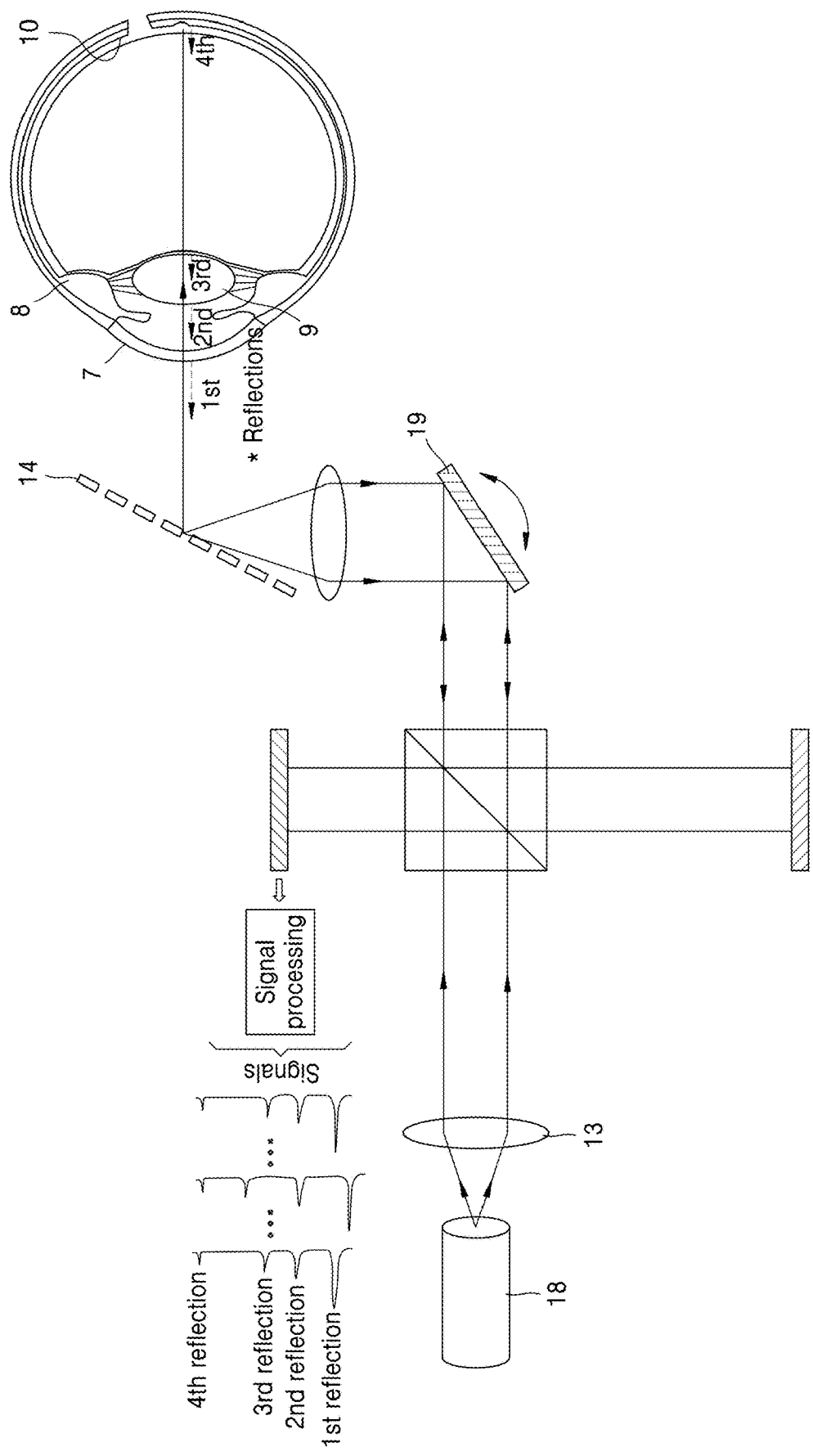
FIG. 12 depicts schematic diagram of an eye accommodation distance determining device according to an embodiment of the disclosure.

FIG. 12 depicts schematic diagram of an eye accommodation distance determining device according to an embodiment of the disclosure.

Referring to FIG. 12, the interferometer of the eye accommodation distance determining device is a two-arm interferometer comprising a single laser 18, a laser driver, an optical-mechanical scanning system, a detector 15, a beam splitter 16, a reference mirror 17 and an optical system.

Fourth embodiment differs from the third one in a method of generating interferometric signal which similar to that of the second embodiment and is not described again The embodiment has more parts, is less compact and more expensive, but provides better signal to noise ratio with the same laser power.

The eye accommodation distance determining device proposed may be used as a part of an adjustable focal length head-mounted display.

Figure 13:
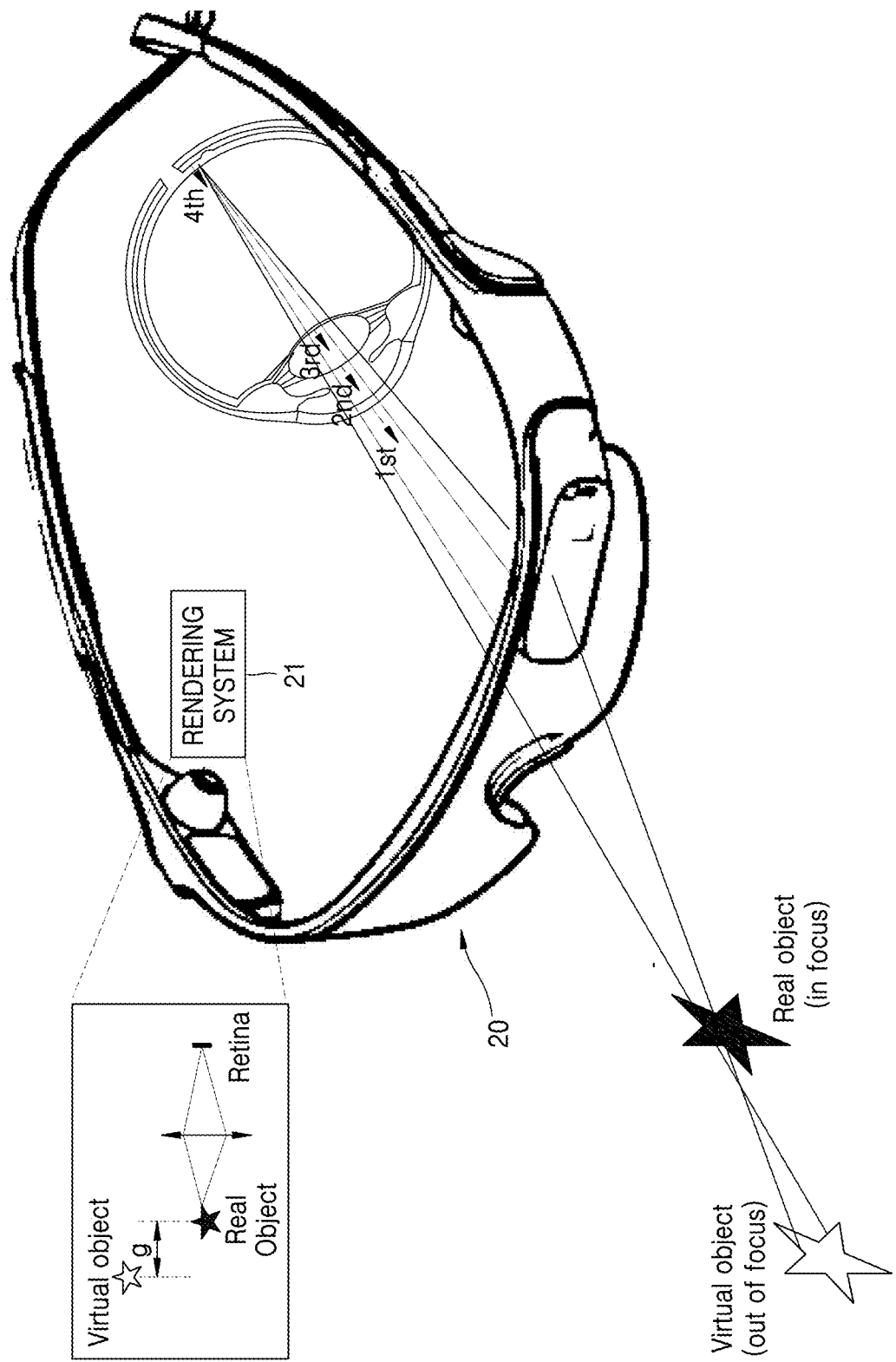
FIG. 13 depicts schematic diagram of a head-mounted display according to an embodiment of the disclosure.

FIG. 13 depicts schematic diagram of a head-mounted display according to an embodiment of the disclosure.

Referring to FIG. 13, the adjustable focal length head-mounted display 20 comprises the eye accommodation distance determining device and an adjustable focal length rendering system 21. The adjustable focal length rendering system 21 is connected with the eye accommodation distance determining device and receives a signal from it about an eye accommodation distance determined by the eye accommodation distance determining device. At the same time, the rendering system 21 is configures to adjust focal length based on the accommodation distance determined. An algorithm for determining the focal length of a visualization system based on the accommodation distance determined depends on the particular application scenario. For example, the rendering system 21 may adjust the focal length so that virtual object displayed are always focused for the user's eye. For example, the rendering system 21 may minimize a gap (g) between a user's eye accommodation distance and a focal plane of a virtual object and adjust a focal length so that the virtual and real objects match each other. Thus, more accurate adjustment of the focal length of the head-mounted display based on the user's eye accommodation distance is provided.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An eye accommodation distance determining device comprising:
   an interferometer configured to:
      generate a plurality of frequency modulated laser beams in different directions, and
      generate a plurality of interferometric signals using laser beams reflected from eye reflecting surfaces among the plurality of frequency modulated laser beams;
   a signal processor configured to generate a signal spectrum using each of the plurality of interferometric signals;
   a distance determiner configured to:
      analyze the signal spectrum, and
      determine distances to the eye reflecting surfaces for each of the plurality of frequency modulated laser beams;
   a point coordinates determiner configured to determine coordinates of points on each of the eye reflecting surfaces for each of the plurality of frequency modulated laser beams based on the determined distances to the eye reflecting surfaces and laser beam direction information;
   a reconstructor configured to generate an eye inner structure model based on the determined coordinates of points on the eye reflecting surfaces; and
   an eye accommodation distance determiner configured to determine, based on the eye inner structure model, an eye accommodation distance.

2. The eye accommodation distance determining device according to claim 1,
   wherein each of signal spectra generated for laser beams falling on a retina of an eye by the signal processor has first to fourth peaks in a frequency domain, and
   wherein the first peak corresponds to a cornea surface, the second peak corresponds to a lens front surface, the third peak corresponds to a lens rear surface, and the fourth peak corresponds to a retina surface.

3. The eye accommodation distance determining device according to claim 2, wherein the distance determiner is further configured to:
   extract peaks according to optical path distances of laser beams from the first to fourth peaks of each of the signal spectra in the frequency domain, and
   calculate distances to the eye reflecting surfaces reflecting each of the plurality of frequency modulated laser beams.

4. The eye accommodation distance determining device according to claim 2,
   wherein the plurality of frequency modulated laser beams fall into different points on the eye reflecting surfaces, and
   wherein the signal processor is further configured to generate signal spectra for the different points on the eye reflecting surfaces using the plurality of frequency modulated laser beams.

5. The eye accommodation distance determining device according to claim 1, wherein the reconstructor is further configured to calculate a cornea curvature radius, a lens front surface curvature radius, a lens rear surface curvature radius, a lens thickness, and a distance between lens and retina by approximating points corresponding to a cornea surface, a lens front surface, and a lens rear surface into spherical surfaces and to determine, based thereon, an eye accommodation distance.

6. The eye accommodation distance determining device according to claim 5, wherein the reconstructor is further configured to determine a direction of an eye optical axis as a direction of a line at which centers of approximating spherical surfaces are located.

7. The eye accommodation distance determining device according to claim 1, wherein the signal processor, the distance determiner, the point coordinates determiner, the reconstructor, and the eye accommodation distance determiner are implemented as single software, a single semiconductor chip, or a single electronic circuit.

8. The eye accommodation distance determining device according to claim 1,
   wherein the interferometer is a self-mixing interferometer comprising a laser array comprising a plurality of lasers and a laser array driver configured to supply each laser of the laser array with a frequency-modulated control signal, and
   wherein the interferometric signal is a laser self-mixing signal.

9. The eye accommodation distance determining device according to claim 1,
   wherein the interferometer is a self-mixing interferometer comprising a laser, a laser driver configured to supply the laser with a frequency-modulated control signal, and an optical-mechanical scanning system, and
   wherein the interferometric signal is a laser self-mixing signal.

10. The eye accommodation distance determining device according to claim 9, wherein the interferometer is configured to direct laser beams, reflected from the eye reflecting surfaces, back to a cavity of a laser emitting the laser beam.

11. The eye accommodation distance determining device according to claim 1,
    wherein the interferometer comprises a laser array comprising a plurality of lasers, a laser array driver configured to supply each laser of the laser array with a frequency-modulated control signal, a detector, a beam-splitter, and a reference mirror, and
    wherein the interferometric signal is a signal generated by the detector.

12. The eye accommodation distance determining device according to claim 1, wherein the interferometer comprises a laser, a laser driver configured to supply the laser with a frequency-modulated control signal, a detector, a beam-splitter, a reference-mirror, and an optical-mechanical scanning system.

13. The eye accommodation distance determining device according to claim 12,
wherein the beam-splitter is configured to divide a laser beam emitted by laser into a first beam and a second beam,
wherein the first beam is reflected from the reference-mirror,
wherein the second beam is reflected from eye reflecting surfaces, and
wherein the reflected first beam and the reflected second beam form an interferometric signal in the detector.

14. An eye accommodation distance determining method comprising:
generating a plurality of frequency modulated laser beams in different directions, wherein a beam direction information corresponds to each of beam direction, and wherein at least part of the plurality of frequency modulated laser beams strike upon reflecting surfaces of an eye inner structure,
generating an interferometric signal for each beam of the plurality of frequency modulated laser beams;
generating a signal spectrum for each interferometric signal of a plurality of interferometric signals;
analyzing the signal spectrum and determining distances to reflecting surfaces for each beam of the plurality of frequency modulated laser beams;
determining, in a coordinate system associated with a head-mounted display, coordinates of points of eye surfaces for each of the beams based on the determined distances to the reflecting surfaces and the beam direction information;
generating an eye inner structure model based on the determined coordinates of points of eye surfaces; and
determining, based on the eye inner structure model, an eye accommodation distance.

15. An adjustable focal length head-mounted display comprising:
an eye accommodation distance determining device comprising:
an interferometer configured to:
generate a plurality of frequency modulated laser beams in different directions, and
generate a plurality of interferometric signals using laser beams reflected from eye reflecting surfaces among the plurality of frequency modulated laser beams,
a signal processor configured to generate a signal spectrum using each of the plurality of interferometric signals,
a distance determiner configured to:
analyze the signal spectrum, and
determine distances to the eye reflecting surfaces for each of the plurality of frequency modulated laser beams,
a point coordinates determiner configured to determine coordinates of points on each of the eye reflecting surfaces for each of the plurality of frequency modulated laser beams based on the determined distances to the eye reflecting surfaces and laser beam direction information,
a reconstructor configured to generate an eye inner structure model based on the determined coordinates of points on the eye reflecting surfaces, and
an eye accommodation distance determiner configured to determine, based on the eye inner structure model, an eye accommodation distance; and
an adjustable focal length rendering system,
wherein the adjustable focal length rendering system is configured to automatically adjust focal length based on an eye accommodation distance obtained from the eye accommodation distance determining device.

* * * * *